US009675321B2

(12) United States Patent
Schlenger

(10) Patent No.: US 9,675,321 B2
(45) Date of Patent: Jun. 13, 2017

(54) ULTRASONOGRAPHIC SYSTEMS AND METHODS FOR EXAMINING AND TREATING SPINAL CONDITIONS

(71) Applicant: Christopher Schlenger, Stockton, CA (US)

(72) Inventor: Christopher Schlenger, Stockton, CA (US)

( * ) Notice: Subject to any disclaimer, the term of this patent is extended or adjusted under 35 U.S.C. 154(b) by 41 days.

(21) Appl. No.: 14/602,566

(22) Filed: Jan. 22, 2015

(65) Prior Publication Data

US 2015/0133785 A1    May 14, 2015

Related U.S. Application Data

(63) Continuation-in-part of application No. 13/713,256, filed on Dec. 13, 2012, now abandoned.

(60) Provisional application No. 61/640,561, filed on Apr. 30, 2012.

(51) Int. Cl.
| | | |
|---|---|---|
| *A61B 8/08* | (2006.01) | |
| *A61B 8/00* | (2006.01) | |
| *A61B 5/00* | (2006.01) | |
| *A61B 8/14* | (2006.01) | |

(52) U.S. Cl.
CPC .......... *A61B 8/0875* (2013.01); *A61B 8/4245* (2013.01); *A61B 8/4263* (2013.01); *A61B 8/466* (2013.01); *A61B 8/483* (2013.01); *A61B 8/5223* (2013.01); *A61B 5/4566* (2013.01); *A61B 8/14* (2013.01); *A61B 8/565* (2013.01)

(58) Field of Classification Search
CPC ..... A61B 8/0875; A61B 8/4263; A61B 8/483; A61B 5/0035; A61B 5/4566
See application file for complete search history.

(56) References Cited

U.S. PATENT DOCUMENTS

| | | | | |
|---|---|---|---|---|
| 5,991,651 A | * | 11/1999 | LaBarbera | ................ A61F 5/04 5/601 |
| 6,587,709 B2 | | 7/2003 | Solf et al. | |
| RE39,133 E | * | 6/2006 | Clayton | ............. A61B 17/7083 600/426 |
| 7,526,071 B2 | * | 4/2009 | Drapeau | .............. A61B 5/0064 378/163 |
| 2006/0176242 A1 | * | 8/2006 | Jaramaz | ............... A61B 5/0059 345/7 |

(Continued)

*Primary Examiner* — Bo J Peng
(74) *Attorney, Agent, or Firm* — Mohr Intellectual Property Law Solutions, PC

(57) ABSTRACT

Methods for assessing spinal health and treatment effectiveness for spinal conditions in a patient via use of an ultrasonagraphic system are shown and described. The ultrasonagraphic system includes optical targets, a transducer probe, an optical tracker unit, an image processing system, a 3D ultrasound processor, and a display. The methods include attaching optical targets to the patient's body; detecting locations of the optical targets on the patient; detecting a location of the transducer probe; moving the transducer probe over at least a portion of the patient's body to collect spinal image data; generating 3D image data; sending 3D image data to the image processing system; processing 3D image data; displaying a real-time 3D image of the one or more vertebrae on the display to allow a healthcare provider to assess spinal health and treatment effectiveness based on the displayed real-time 3D image.

18 Claims, 5 Drawing Sheets

(56) References Cited

U.S. PATENT DOCUMENTS

| | | | |
|---|---|---|---|
| 2010/0086185 A1* | 4/2010 | Weiss | B60R 25/00 |
| | | | 382/131 |
| 2011/0021914 A1* | 1/2011 | Zheng | A61B 5/103 |
| | | | 600/443 |
| 2011/0213221 A1* | 9/2011 | Roche | A61B 5/0031 |
| | | | 600/301 |

* cited by examiner

ULTRASONOGRAPHIC SYSTEMS AND METHODS FOR EXAMINING AND TREATING SPINAL CONDITIONS

CROSS REFERENCE TO RELATED APPLICATIONS

This application claims priority to and is a continuation-in-part of copending U.S. application Ser. No. 13/713,256, filed on Dec. 13, 2012, which is hereby incorporated by reference for all purposes. U.S. patent application Ser. No. 13/713,256 claims priority to and the benefit under 35 U.S.C. §119(e) of U.S. Provisional Patent Application, Ser. No. 61/640,561, filed on Apr. 30, 2012, which is hereby incorporated by reference for all purposes.

BACKGROUND

The present disclosure relates generally to ultrasound imaging systems and methods. In particular, ultrasonographic systems and methods for examining and treating spinal conditions are described.

Various techniques for acquiring images of subcutaneous body structures, such as tendons, muscles, vessels, internal organs, and bone surfaces, are in use today by medical practitioners. Known techniques include x-ray, magnetic resonance imaging (MRI), and radionuclide imaging. X-ray and radionuclide imaging techniques suffer from the drawback of exposing patients to potentially harmful ionizing radiation. MRI techniques can be expensive and therefore unavailable to some patients as a diagnostic tool. Further, MRI is unsatisfactorily slow and provides low resolution images of bone structures.

Another technique for imaging subcutaneous body structures as a diagnostic aid involves using ultrasonographic systems. Ultrasound devices used in ultrasonographic systems produce sound waves at a frequency above the audible range of human hearing, which is approximately 20 kHz. Sound waves between 2 and 18 Mhz are often used for ultrasound medical diagnostic applications. At present, there are no known long term side effects from interrogating the human body with ultrasound waves.

Acquiring images of the spine is one known application for ultrasonographic systems. However, known ultrasonographic systems for spinal examination and treatment are not entirely satisfactory for the range of applications in which they are employed.

For example, existing ultrasound technology does not have the ability to readily recreate three dimensional representations of bone structures. Further, conventional ultrasound systems do not enable the user to re-identify the position of bone structures externally. Moreover, current ultrasonographic systems generally only represent soft tissue structures in three dimensional space and do not satisfactorily represent bone structures in three dimensions.

Further limitations of conventional ultrasonographic systems relate to their reliance on magnetic positioning systems as opposed to more precise optical tracking systems to determine the patient's and/or the ultrasound transducer's position in space. Compounding the relative imprecision of conventional ultrasonographic systems is the fact that they generally determine position data relative to fixed objects adjacent to the patient, such as chest boards the patient is resting on, rather than relative to targets on the patient's body itself. The precision limitations of current ultrasonographic systems mean that practitioners must rely on external landmarks on the body to locate vertebra in need of treatment, which is prone to error.

Known ultrasonographic systems are typically not configured to automatically match new images of a patient's spine to previously acquired images of the patient's spine. The inability of conventional systems to effectively register new spinal images with previously acquired spinal images limits the practitioner's ability to accurately compare a given segment of the spine over time and to evaluate treatment effectiveness.

How acquired images are displayed by conventional ultrasonographic systems highlights another limitation of conventional systems. For example, conventional systems characteristically display acquired images on a two-dimensional screen. Even systems capable of representing acquired images in three-dimensional space generally do so on a two-dimensional screen, with the associated inherent limitations, and lack means to stereoscopically display the images in three-dimensional space.

Another drawback of conventional systems to examine and treat spinal conditions with ultrasound equipment relates to their inability to adequately extrapolate motion of the spine. Often, conventional ultrasonographic systems are limited to static images of the spine without an effective way to correlate different images of the spine when the patient moves to different positions. The inability to correlate images of the spine in different positions deprives the practitioner of important information regarding how the vertebrae move when flexing, extending, and/or rotating.

Thus, there exists a need for ultrasonographic systems that improve upon and advance the design of known ultrasonographic systems. Examples of new and useful ultrasonographic systems relevant to the needs existing in the field are discussed below.

Disclosure addressing one or more of the identified existing needs is provided in the detailed description below. An example reference relevant to ultrasonographic systems includes U.S. Patent Publication 20110021914. The complete disclosure of the referenced patent application publication is herein incorporated by reference for all purposes.

SUMMARY

The present disclosure is directed to methods for assessing spinal health and treatment effectiveness for spinal conditions in a patient via use of an ultrasonagraphic system. The ultrasonagraphic system includes optical targets, a transducer probe, an optical tracker unit, an image processing system, a 3D ultrasound processor, and a display. The methods include attaching optical targets to the patient's body; detecting locations of the optical targets on the patient; detecting a location of the transducer probe; moving the transducer probe over at least a portion of the patient's body to collect spinal image data; generating 3D image data; sending 3D image data to the image processing system; processing 3D image data; displaying a real-time 3D image of the one or more vertebrae on the display to allow a healthcare provider to assess spinal health and treatment effectiveness based on the displayed real-time 3D image.

DETAILED DESCRIPTION

The disclosed ultrasonagraphic systems and methods will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of ultrasonagraphic system and method examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Figure 1:
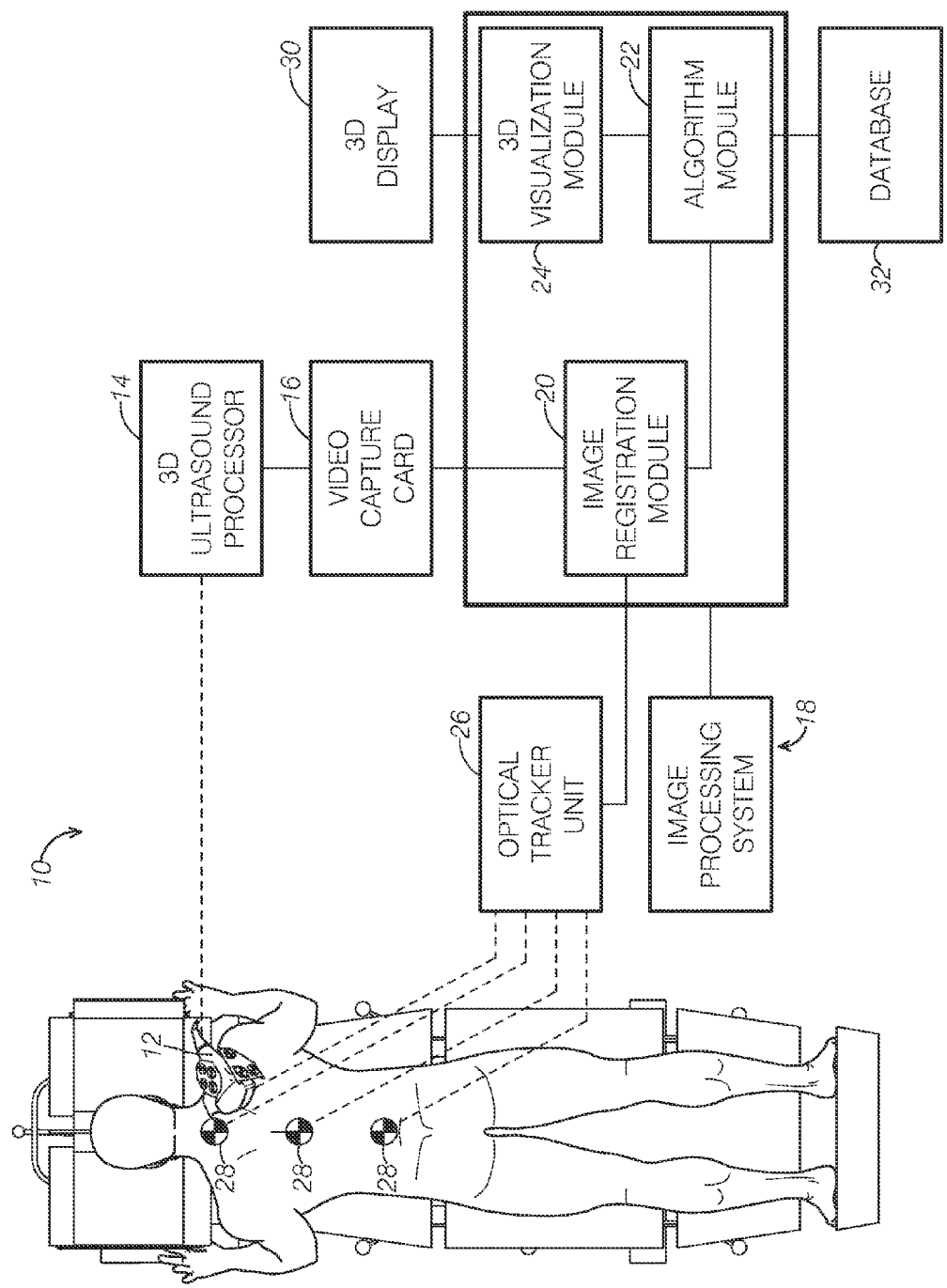
FIG. 1 is a schematic view of an ultrasonagraphic system for examining and treating spinal conditions consistent with the present invention.

With reference to FIG. 1, an ultrasonagraphic system 10 for assessing spinal health and treatment effectiveness of spinal conditions will be described. The components of ultrasonagraphic system 10 will be listed and then explained in more detail below. As shown in FIG. 1, ultrasonagraphic system 10 can include an ultrasound transducer probe 12, a three-dimensional ultrasound processor 14, a video capture card 16, an image processing system 18, an optical tracker unit 26, optical targets 28, a stereoscopic three-dimensional display 30, and a database 32. Image processing system 18 includes an image registration module 20, an algorithm module 22, and a three-dimensional visualization module 24. In some examples, the video capture card can be excluded from the, ultrasonagraphic system.

Before discussing the components of ultrasonagraphic system 10 in detail, some of the functions and capabilities of the system as a whole will be described to provide context to the system. As a variety of system examples are contemplated, the reader should understand that different system examples will provide different combinations of features and operating characteristics.

Ultrasonagraphic system 10 of FIG. 1 is configured to enable a practitioner to acquire images of a patient's spine in real-time with ultrasound transducer probe 12 and processor 14 without subjecting the patient to potentially harmful ionizing radiation. Further, ultrasonagraphic system 10 of FIG. 1 enables a practitioner to acquire images of the outer cortex of a patient's spine with high resolution on a real-time or substantially real-time basis.

Moreover, the ultrasonagraphic systems described herein are configured to automatically process acquired images of a user's spine into three dimensional images with the three-dimensional ultrasound system and imaging processing system 18. In some examples, the system is configured to stereoscopically display the images in three dimensions, such as with the 3D visualization module and the 3D stereoscopic display shown in FIG. 1.

As shown in FIG. 1, ultrasonagraphic system 10 utilizes optical tracking technology in the form of optical tracking unit 26 and optical targets 28 to precisely detect the patient's and ultrasound transducer probe's 12 position in space. However, additionally or alternatively to the optical tracking technology included in the example of FIG. 1, the ultrasonagraphic system may include magnetic positioning systems or attitude heading reference systems to detect the position of the patient, the transducer, or both. It is worth noting that that system 10 of FIG. 1 is configured to detect the position of the patient directly by the optical target positioned on the patient as opposed to merely detecting the position of a fixed object near the patient, such as a chest board or other stationary reference objects.

Additionally or alternatively, the ultrasonographic system may include an infrared scanning system configured to scan illuminated objects, such as patients, in three-dimensions. The infrared scanning system may include an infrared light projector, a camera or CMOS image sensor to detect the infrared light interacting with illuminated objects, and a microchip including computer executable instructions for spatially processing scanned objects. Suitable infrared scanning systems include the Light Coding™ system included in the Kinect™ gaming system. The infrared scanning system may supplement the optical tracking device and optical targets described above or may replace them in some applications.

Ultrasonagraphic system 10 of FIG. 1 affords the practitioner with highly precise information about the patient's position and the position of ultrasound transducer probe 12. Further, system 10 provides the practitioner with substantially real-time three dimensional images of a patient's spine by processing images generated by the 3D Ultrasound system with image processing system 18 and displaying them on 3-D display 30. By combining precise position data and substantially real-time spinal image data, the inventive ultrasound systems described herein allow the practitioner to accurately locate internal features on a patient's spine, such as a particular vertebra in need of treatment. In fact, the systems described in this application enable a practitioner to locate internal features without having to rely on external landmarks on the body, which is a technique prone to error.

While certain examples of ultrasonic systems described herein display acquired images on a two-dimensional screen, system 10 of FIG. 1 stereoscopically displays acquired images in three-dimensional space. Stereoscopically displaying adages of a patient's spine in three-dimensional space enables the practitioner to more accurately examine and treat the patient's spine.

Ultrasonagraphic system 10 of FIG. 1 is configured to automatically match new images of a patient's spine to previously acquired images of the patient's spine stored in database 32 with image registration module 20. The ability of system 10 in FIG. 1 to effectively register new spinal images with previously acquired spinal images allows a practitioner to accurately compare a given segment of the spine over time and to evaluate treatment effectiveness.

Ultrasonagraphic system 10 of FIG. 1 configured to interpolate and/or extrapolate motion of the spine when the patient moves to different positions. System 10 interpolates and extrapolates spinal motion by registering different images of the spine acquired by ultrasound processor 14 to a common reference frame with image registration module 20. The ability of ultrasonagraphic system 10 to correlate images of the spine in different positions provides the practitioner with important information regarding how the patient's vertebrae move when flexing, extending, and/or rotating.

With reference to FIG. 1 the reader can see that ultrasonagraphic system 10 includes an ultrasound system having transducer probe 12 and a 3D ultrasound processor 14. Transducer probe 12 is in data communication with 3D ultrasound processor 14. In some examples, the 3D ultrasound processor is supported within the transducer probe and in other examples the components are separate from one another. Any conventional or later developed means of data communication between the transducer and the 3D ultrasound processor may be employed, such as wired communication and wireless communication.

Transducer probe 12 will in many examples be of a size suitable to be held in a practitioner's hand and moved over the patients spine. Further, transducer probe 12 is configured to receive a plurality of optical targets 28 that aid optical tracker unit 26 in determining transducer probe's 12 positioning in space. The practitioner may move the transducer probe 12 over the entire posterior aspect of the spine or just an area of interest. In a known manner, transducer probe 12 interrogates the patients spine with high frequency sound waves as schematically depicted in FIG. 1.

3D ultrasound processor 14 receives data from transducer probe 12 and generates three-dimensional images based on the data from transducer probe 12. In some examples, the system includes a 2D ultrasound processor instead of or in addition to the 3D ultrasound processor. The images generated by 3D ultrasound processor 14 are sent to video Capture card 16.

From video capture card 16, the three dimensional images generated by ultrasound processor 14 are sent to image processing system 18. In particular, as shown in FIG. 1, the images are sent to image registration module 20 of image processing system 18. Image registration module 20 is configured to correlate different images to a common reference frame. Any conventional or later developed image registration module may be used. In examples excluding the video capture card, the video can be sent directly (i.e., a direct feed) from the 3D ultrasound processor to the image processing system.

Working in conjunction with image registration module 20 is algorithm module 22 of image processing system 18. Algorithm module 22 includes computer-executable instructions (i.e., computer-readable instructions) for coordinating the flow of data through image processing system 18 and to components in data communication with image processing system 18. For example, algorithm module 22 includes computer executable instructions for polling the database for previously acquired images and for sending registered image data to database 32 to be stored for later use. Additional instruction sets that may be programed into the algorithm include instructions for delivering resolved image data to 3D visualization module 24 and/or for coordinating data inputs from optical tracker 26.

Further, algorithm module 22 includes computer-readable instructions for calibrating and/or recalibrating ultrasonagraphic system 10. Specifically, images that are transmitted from the ultrasound equipment can be calibrated for time and space. There is normally a small lag between the processing of the images from the 3D ultrasound processor into the image processing system where the images are stitched together. Thus, this lag time can be accounted for via calibration of the ultrasonagraphic system. The images that are fed from 3D ultrasound processor can also be calibrated for space. For example, the ultrasound images are sent usually as pixels, which then need to be converted to size measurements. This allows more accurate reconstruction of the images for measuring purposes.

Furthermore, parameters on ultrasound equipment, such as depth and zoom, will change the relation from the pixel distance to actual size with every adjustment. In one example, there can be several points of calibration performed at different depths, degrees of zoom, and/or other parameters that can affect the calibration. The algorithm module can include computer-readable instructions for an algorithm to extrapolate how the calibration will change based upon the changes to the specific parameter so that there can be a continuous acquisition of images that would otherwise require stopping the procedure for recalibration.

3D visualization module 24 may be any conventional or later developed software and/or hardware for generating three-dimensional visual data for display on a display device. In the example shown in FIG. 1, 3D visualization module 24 is configured to generate stereoscopic three-dimensional visual data for display on a device configured to stereoscopically display three-dimensional images. 3D display 30 may include any conventional or later developed accessories for stereoscopic viewing of three-dimensional images, including 3D glasses and the like.

As shown in FIG. 1, optical tracker unit 26 is configured to optically track the position of one or more optical targets 28. Optical tracking devices 26 may be any known or later developed devices for detecting and correlating the position of optical targets 28, such as multiple two-dimensional imaging sensors or cameras.

In addition, optical tracker unit 26 is configured to determine the position of optical targets 28 as they move through space. In particular, optical tracker unit 26 is configured to determine the position of optical targets 28 about three axes and with six degrees of freedom. Optical tracker unit,nay Include multiple image sensors (not shown) and be configured to calculate the location of every optical target 28 through geometric triangulation. When more than two markers are grouped together to form a rigid-body target, it becomes possible to determine the target's orientation, yielding a total of six degrees of freedom.

Optical targets 28 may be conventional, specially developed, or later developed targets configured to cooperate with optical tracking unit 26. In some examples, the optical targets extend in three dimensions about three coordinate axes and include distinct targets representing each axis. In other examples, the optical target extends in three dimensions about six axes and includes distinct targets representing each of the six axes. The optical targets may be active, such as by emitting infrared signals to the optical target, or passive, such as including retro-reflective markers affixed to some interaction device.

Any number of optical targets 28 may be employed, with more optical targets 28 being used generally increasing the precision of the positional data. However, fully satisfactory results may be obtained with two optical targets 28. In some examples, a single optical target is used.

Additionally or alternatively, the ultrasonographic s, stem may include precision-augmented tracking modules or optical tracker units when relaying positional data of the transducer probe and optical trackers back to the optical tracker unit. Such optical tracker units may employ solid-state gyroscopes to achieve this added measure of precision.

Figure 3:
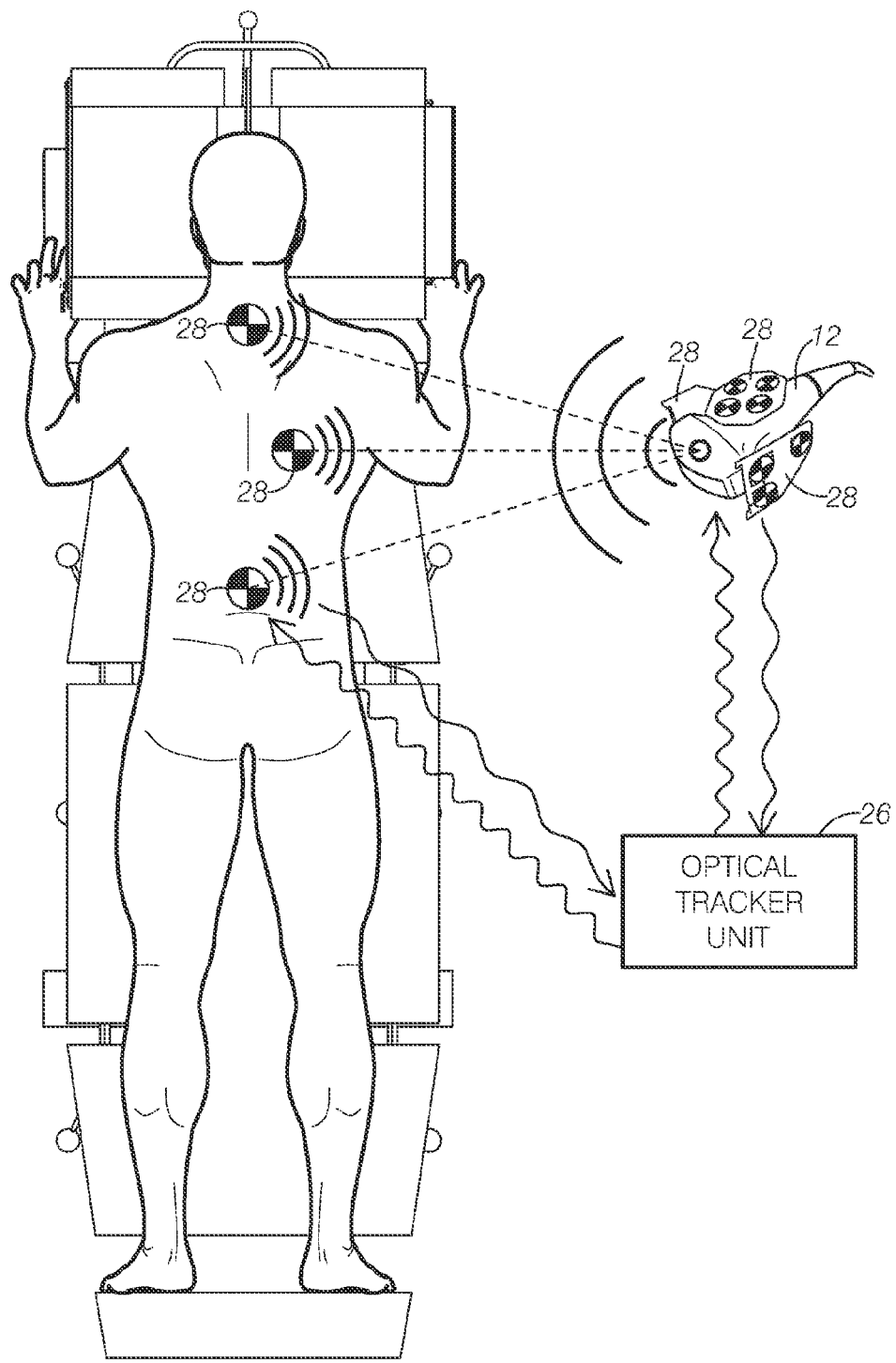
FIG. 3 is a perspective view of an ultrasound transducer probe and optical targets.
Figure 4:
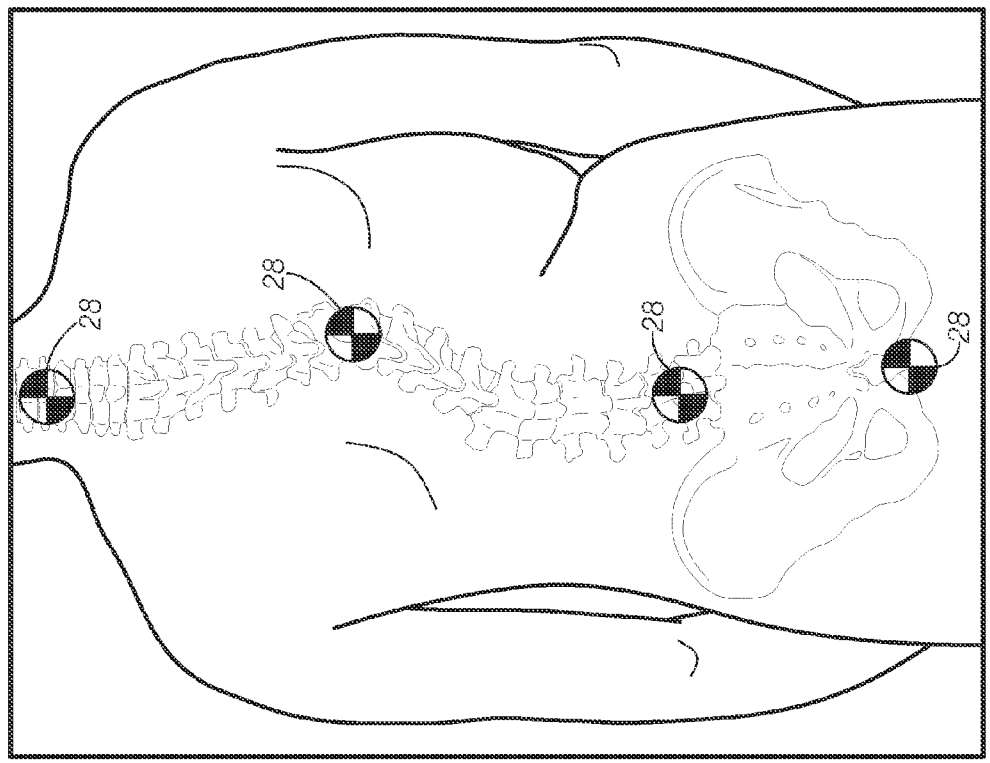
FIG. 4 is a view of the optical targets placed on the spine of a patient.
Figure 5:
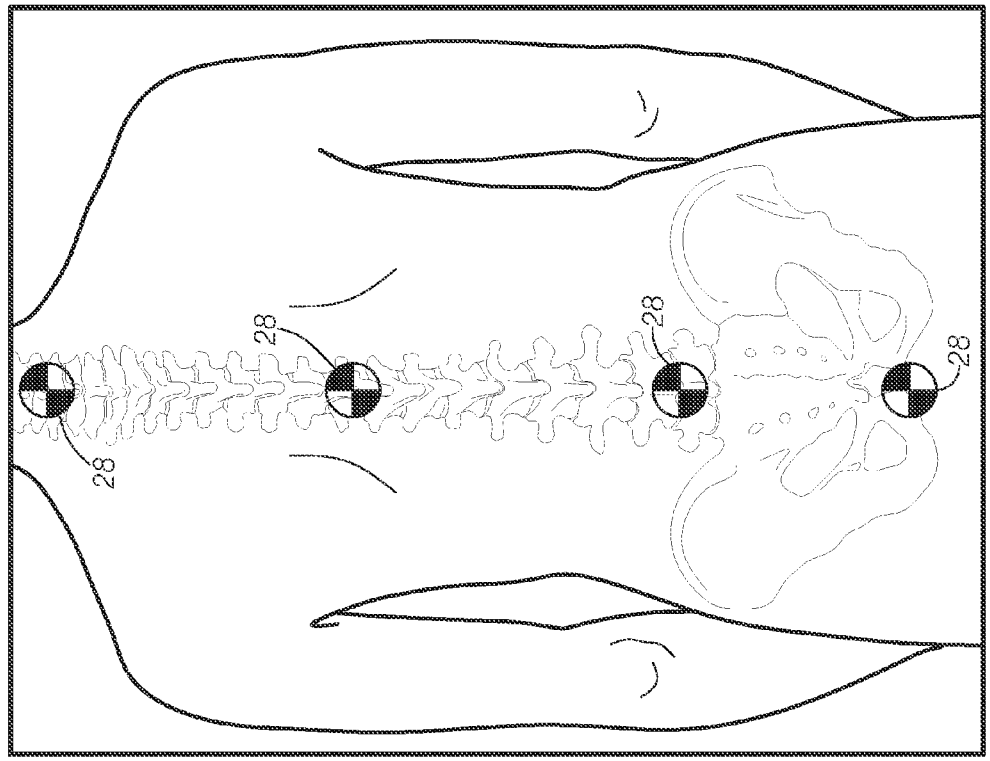
FIG. 5 is a view of the optical targets placed on the spine of a patient.

Turning attention to FIGS. 4 and 5, when ultrasonographic system 10 is utilized, the patient will have a plurality of optical targets 28 affixed to a desired location on the patient's back and there will be at least one optical target 28 attached to the transducer probe 12. The patient will be positioned on a specially configured mechanical table (see FIGS. 1 and 3), that allows the patient to be partially standing, yet still supported. The specially configured table enables the patient to be in a weight bearing, but still and stationary position during the imaging process. In sonic examples, the patient is instructed to move his torso to different positions to enable the practitioner to acquire images of the patient's spine in different positions and to interpolate and/or extrapolate motion of the spine.

As can be seen in FIG. 3, optical tracker unit 26 will detect the position of optical targets 28 affixed to the patient and the position of optical targets 28 affixed to transducer probe 12. The position data will be sent to image registration module 20 to correlate the position of the transducer probe 12 relative to the position of the patient in space. The position data will be further correlated to the images of the patient's vertebra in acquired images with image processing system 18.

One example of optical targets 28 being placed in various locations along the patient's spine is depicted in FIG. 4. The patient's spine is in a fixed position and the patient refrains from any movement or contortion of their body while resting in the specially configured mechanical table. An ultrasonographic scan of the patient's spine with ultrasound transducer probe 12 would register an image of the patient's spine as being substantially straight as shown in FIG. 4.

Referring now to FIG. 5, optical targets 28 can be seen in the same position along the patient's spine; however, the patient has now moved or contorted their spine from the substantially straight position shown in FIG. 4. Ultrasound transducer probe 12 is able to track this movement information in real-time for image processing by image processing system 18.

The real-time processing of positional information by system 10 allows for focused treatment based on 3D stereoscopic images of the patient's spine. Further, system 10 aids the practitioner in reviewing current and past images, which allows for frequent changes in the patient's treatment plan as opposed to waiting months for results obtained through other conventional methods.

In some examples, prior images of a patient's spine will be compared with more recent images of the spine to determine treatment effectiveness and how well the patient is healing over time. The algorithm module and the image registration module may cooperate to correlate the images acquired at different times with high precision. In particular, the position data of one acquired image may be precisely mapped with the position data of another image to enable the practitioner to readily correlate the anatomical position of each image and have confidence that each image corresponds to the same interior anatomical feature of the patient. In this manner, the practitioner need not rely on external landmarks on the patient's body to correlate different images over time, which can lead to errors.

Figure 2:
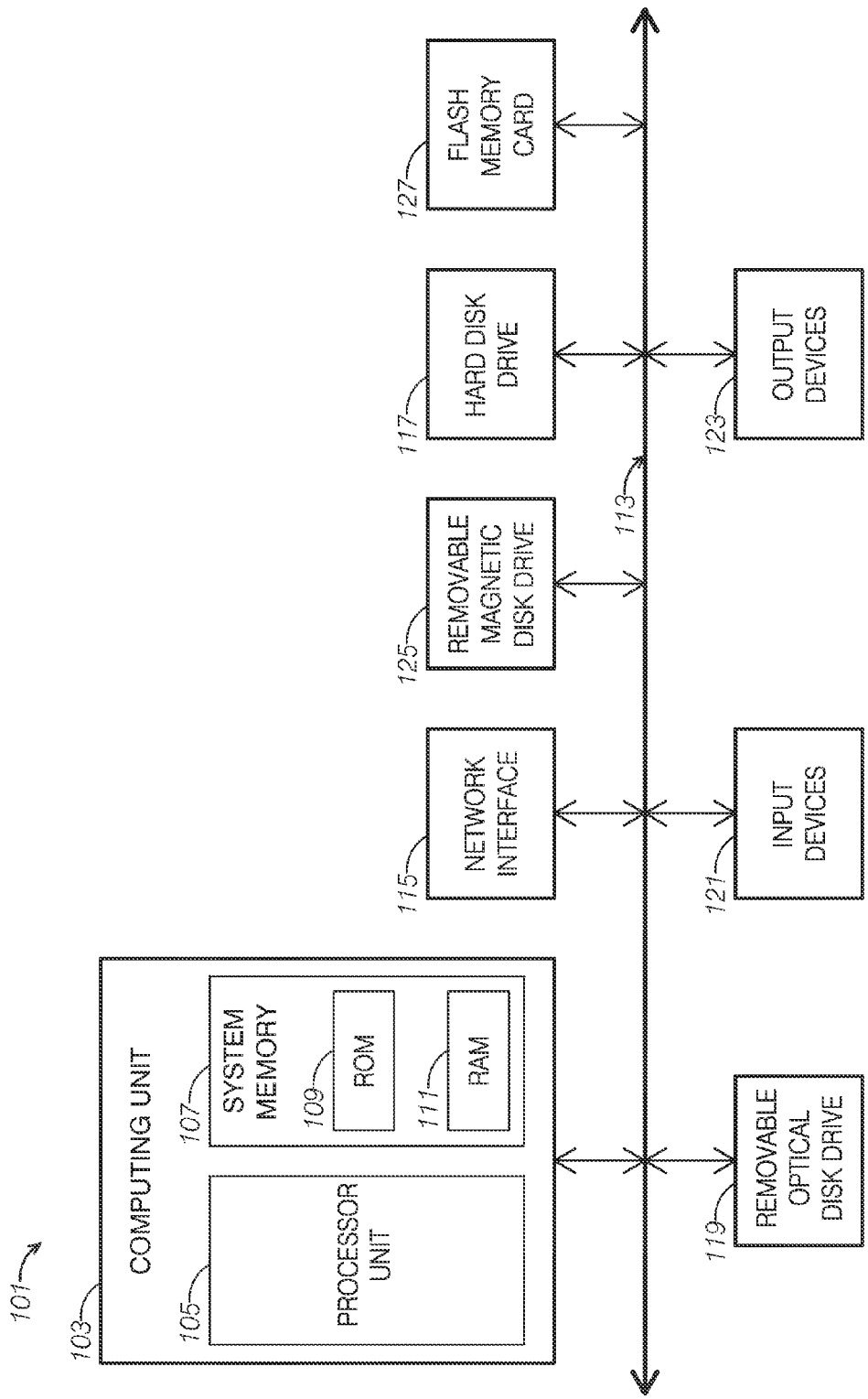
FIG. 2 is a schematic view of a programmable computing device component of an image processing system of the ultrasonagraphic systems described herein.

Turning attention to FIG. 2, a programmable computing device suitable for use as part of the image processing system will be described. While the following paragraphs describe one suitable example of an image processing system, the reader will understand that many different examples are contemplated. For example, image processing system 18 could include an embedded software system, a standalone personal computer, and/or a networked computer system.

Networked computer systems may suffer from bandwidth limitations with conventional network infrastructures, but future developments will likely alleviate those bandwidth issues. Standalone personal computers may not always providing the processing power to manage the data processing involved with the ultrasonographic systems described above. However, processing power improvements will certainly enable personal computers to handle the data processing involved in ultrasonographic systems described herein.

From the above discussion of ultrasonographic systems, those skilled in the art will recognize that various examples of the image processing system may be implemented using electronic circuitry configured to perform one or more functions. For example, with some embodiments of the invention, the image processing system may be implemented using one or more application-specific integrated circuits (ASICs). In some examples, however, components of various examples of the invention will be implemented using a programmable computing device executing firmware or software instructions, or by some combination of purpose-specific electronic circuitry and firmware or software instructions executing on a programmable computing device.

Accordingly, FIG. 2 shows one illustrative example of a computer 101 that can be used to implement various embodiments of the invention. As seen in this figure, computer 101 has a computing unit 103. Computing unit 103 typically includes a processing unit 105 and a system memory 107. Processing unit 105 may be any type of processing device for executing software instructions, but will conventionally be a microprocessor device. System memory 107 may include both a read-only memory (ROM) 109 and a random access memory (RAM) 111. As will be appreciated by those of ordinary skill in the art, both read-only memory (ROM) 109 and random access memory (RAM) 111 may store software instructions to be executed by processing unit 105.

Processing unit 105 and system memory 107 are connected, either directly or indirectly, through a bus 113 or alternate communication structure to one or more peripheral devices. For example, processing unit 105 or system memory 107 may be directly or indirectly connected to additional memory storage, such as a hard disk drive 117, a removable optical disk drive 119, a removable magnetic disk drive 125, and a flash memory card 127. Processing unit 105 and system memory 107 also may be directly or indirectly connected to one or more input devices 121 and one or more output devices 123. Input devices 121 may include, for example, a keyboard, touch screen, a remote control pad, a pointing device (such as a mouse, touchpad, stylus, trackball, or joystick), a scanner, a camera or a microphone. Output devices 123 may include, for example, a monitor display, an integrated display, television, printer, stereo, or speakers.

Still further, computing unit 103 will be directly or indirectly connected to one or more network interfaces 115 for communicating with a network. This type of network interface 115, also sometimes referred to as a network adapter or network interface card (NIC), translates data and control signals from computing unit 103 into network messages according to one or more communication protocols, such as the Transmission Control Protocol (TCP), the Internet Protocol (IP), and the User Datagram Protocol (UDP).

These protocols are well known in the art and thus will not be discussed here in more detail. An interface 115 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 will often be connected to the 3D ultrasound processor and transducer system. In addition to a 3D ultrasound unit, computer 101 may be connected to or otherwise include one or more other peripheral devices, such as a telephone.

The telephone may be, for example, a wireless "smart phone," such as those featuring the. Android or iOS operating systems. As known in the art, this type of telephone communicates through a wireless network using radio frequency transmissions. In addition to simple communication functionality, a "smart Phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with computer 101 so that their data maintained may be synchronized.

Of course, still other peripheral devices may be included with or otherwise connected to a computer 101 of the type illustrated in FIG. 2, as is well known in the art. In some cases, a peripheral device may be permanently or semi-permanently connected to computing unit 103. For example, with many computers, computing unit 103, hard disk drive 117, removable optical disk drive 119 and a display are semi-permanently encased in a single housing.

Still other peripheral devices may be removably connected to computer 101, however. Computer 101 may include, for example, one or more communication ports through which a peripheral device can be connected to computing unit 103 (either directly or indirectly through bus 113). These communication ports may thus include a parallel bus port or a serial bus port, such as a serial bus port using the Universal Serial Bus (USB) standard or the IEEE 1394 High Speed Serial Bus standard (e.g., a Fire-wire port). Alternately or additionally, computer 101 may include a wireless data "port," such as a Bluetooth ® interface, a Wi-Fi interface, an infrared data port, or the like.

It should be appreciated that a computing device employed according various examples of the invention may include more components than computer 101 illustrated in FIG. 2, fever components than computer 101, or a different combination of components than computer 101. Some implementations of the invention, for example, may employ one or more computing devices that are intended to have a very specific functionality, such as a server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Figure 6:
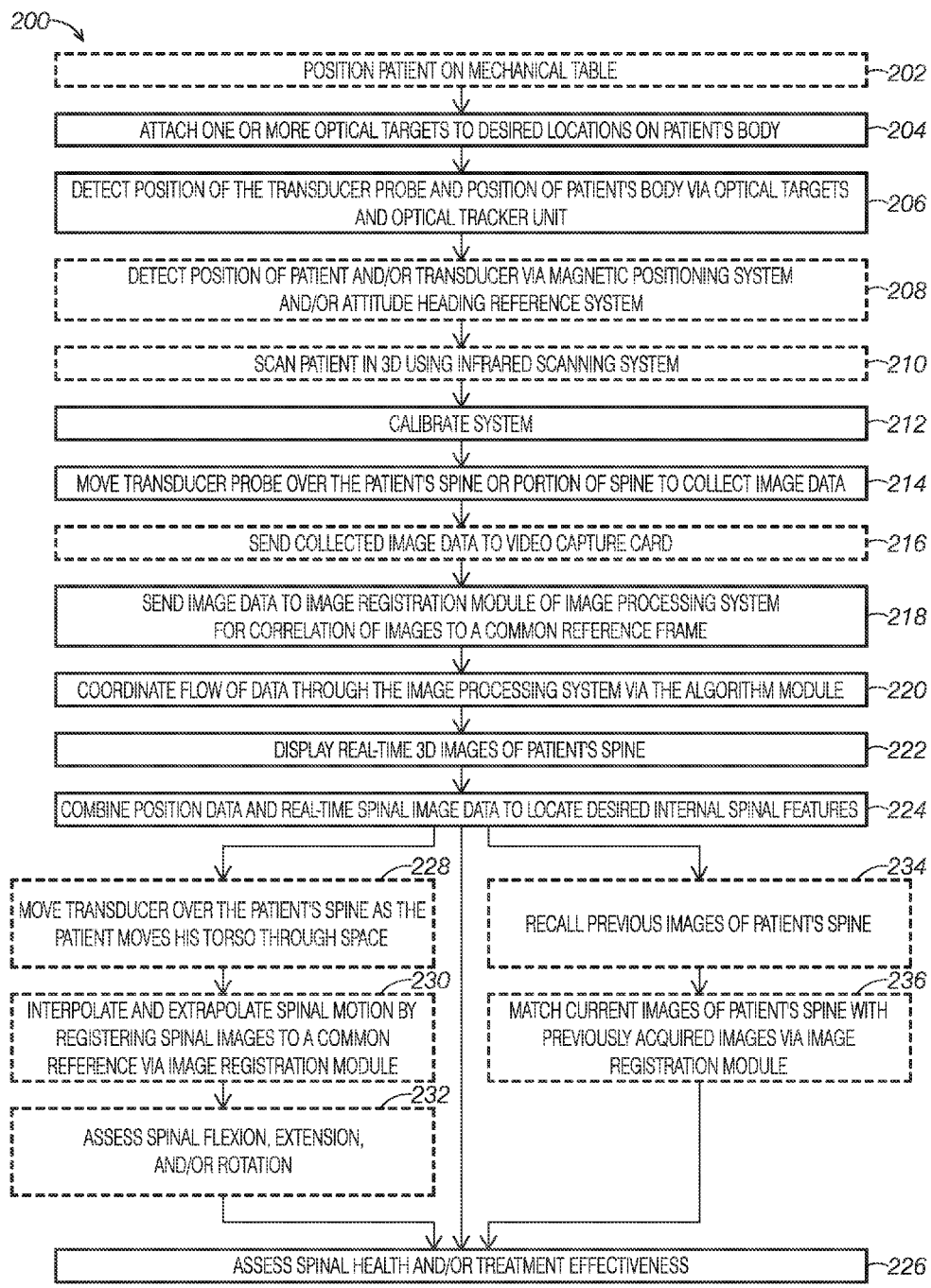
FIG. 6 is a flow diagram of an example method for using the presently described ultrasonagraphic system.

Finally, FIG. 6 shows an example method, method 200, for using the presently described ultrasonagraphic system for assessing spinal health and treatment effectiveness of spinal conditions. First, at step 202, method 200 includes optionally positioning a patient on the above described mechanical table. In other examples, the patient can be positioned in a standing position, a lying prone position, a seated position, etc.

After positioning of the patient, one or more optical targets are attached to desired locations on the patient's body at step 204. A position of the transducer probe and a position of the patient's body are detected via the optical targets (i.e., one or more optical targets attached to the patient's body and one or more optical targets attached to the transducer probe) and the optical tracker unit at steps 206. Optionally, a position of the patient and/or a position of the transducer probe can additionally be detected via a secondary detection mechanism, such as a magnetic positioning system and/or an attitude heading reference system at step 208. Further, the patient can optionally be scanned in 3D using an infrared scanning system at step 210.

Next, at step 212, the ultrasonagraphic system is calibrated for time, space, and/or parameters of the ultrasound equipment. The operator then moves the transducer over the patient's body at a location that corresponds to the patient's spine to collect image data at step 214. The image data is sent to the video capture card at step 216. It will be appreciated that in ultrasonagraphic systems excluding a video capture card, the image data is directly send to the image processing system. Accordingly, image data is sent to the image registration module of the image processing system for correlation of images to a common reference point at step 218.

At step 220, the algorithm module coordinates the flow of data through the image processing system. Next, real-time 3D images of the patient's spine are displayed on a display of the ultrasonagraphic system at step 222. The real-time 3D spinal image data can then be combined with position data so that the operator can locate desired internal spinal features at step 224. In some examples, the operator can use this information to assess spinal health and/or treatment effectiveness at step 226.

Additionally or alternatively, in other examples, the operator can collect additional data and/or compare current images to previous images to assess spinal health and/or treatment effectiveness. Specifically, in a first example, the transducer probe is moved over or held over the patient's spine as the patient moves through space at step 228. This allows the ultrasonagraphic system to collect image data reflecting flexion, extension, and/or rotation of the patient's spine. Next, at step 230, interpolation and/or extrapolation of spinal motion is determined by registering the flexion, extension, and/or rotation image data to a common reference point via the image registration module. The operator can then assess spinal flexion, extension, and/or rotation at step 232 in order to assist in assessment of spinal health and/or treatment effectiveness at step 220.

Further, in another example, the ultrasonagraphic system can be used to recall previous images of the patient's spine at step 234. The previous images can be stored in the computer s stern of the ultrasonagraphic system and/or a database. The system then matches current 3D images of the patient's spine with previously acquired images via the image registration module. In this example, the compared images can be used to assist the operator in assessment spinal health and/or treatment effectiveness in step 226.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims whether they are directed to the same invention or a different invention and whether they are different, broader, narrower or equal in scope to the original claims, are to be considered within the subject matter of the inventions described herein.

The invention claimed is:

1. A method for assessing spinal health and treatment effectiveness for spinal conditions of a patient via use of an ultrasonagraphic system, the ultrasonagraphic system having one or more patient optical targets that are attachable to a patient's body, a transducer probe having one or more transducer optical targets, an optical tracker unit, an image processing system, a 3D ultrasound processor, and a display, the one or more patient optical targets and the one or more transducer optical targets being in data communication with an optical tracker unit, the transducer probe being in data communication with the 3D ultrasound processor and configured to detect locations of one or more vertebrae of the patient, the method comprising:
attaching one or more patient optical targets to desired positions on the patient's body;
detecting locations of the one or more patient optical targets via the optical tracker unit;
detecting a location of the transducer probe via the one or more transducer optical targets and the optical tracker unit;
moving the transducer probe over at least a portion of the patient's body to collect spinal image data while the patient is moving through space to collect one or more of flexion, extension, and rotation image data of the one or more vertebrae;
tracking the movement of the patient via the patient optical targets attached to the patient's body and correlating the movement of the patient with the collected spinal image data;
generating 3D image data via the 3D ultrasound processor;
sending 3D image data to the image processing system;
processing 3D image data via the image processing system;
displaying a real-time 3D image of the one or more vertebrae on the display to allow a healthcare provider to assess spinal health and treatment effectiveness based on the displayed real-time 3D image.

2. The method of claim 1, further comprising positioning the patient on a mechanical table that allows the patient to be partially weight-bearing and partially-supported, prior to attaching the one or more patient optical targets to the patient's body.

3. The method of claim 1, further comprising detecting a position of one or more of the patient's body and the transducer via a magnetic positioning system.

4. The method of claim 1, further comprising:
scanning the patient's body in 3D using an infrared scanning system to produce infrared image data; and
spatially processing the infrared image data to track the movement of the patient.

5. The method of claim 1, wherein processing image data via the imaging processing system further comprises: sending image data from the video capture card to an image registration module of the image processing system, and
correlating image data to a common reference frame.

6. The method of claim 5, wherein correlating image data to the common reference frame comprises correlating a position of the transducer probe relative to a position of the patient in space and to image data of the one or more vertebrae.

7. The method of claim 1, further comprising coordinating a flow of 3D image data through the image processing system, the optical tracker unit, the 3D ultrasound processor, the video capture card, the image registration module, a 3D visualization module of the image processing system, and a database via an algorithm module of the image processing system.

8. The method of claim 7, wherein coordinating the flow of image data via the algorithm module comprises one or more of coordinating data inputs from the optical tracker module, delivering resolved images to a 3D visualization module of the image processing system, polling of a database for previously acquired images of the one or more vertebrae, and sending image data to the database for storage.

9. The method of claim 1, wherein displaying the real-time 3D image of the one or more vertebrae on the display comprises stereoscopically displaying the real-time 3D image of the one or more vertebrae on the display via a 3D visualization module of the processing system.

10. The method of claim 1, further comprising combining position data and the real-time 3D image of the one or more vertebrae to allow the healthcare provider to locate targeted internal spinal features.

11. The method of claim 1, further comprising interpolating and extrapolating spinal motion via registering flexion, extension, and rotation image data of the one or more vertebrae to a common reference point via an image registration module of the image processing system.

12. The method of claim 1, further comprising correlating images of the spine in different positions to a common reference point via an image registration module of the image processing system.

13. The method of claim 1, further comprising recalling previous image data of the patient's spine stored in a database.

14. The method of claim 13, further comprising automatically matching current image data with the previous image data to a common reference point via an image registration module of the image processing system to allow the healthcare provider to assess the one or more vertebrae over time.

15. A method for assessing spinal health and treatment effectiveness for spinal conditions of a patient via use of an ultrasonagraphic system, the ultrasonagraphic system having one or more patient optical targets that are attachable to a patient's body, a transducer probe having one or more transducer optical targets, an optical tracker unit, an image processing system, a 3D ultrasound processor, and a display, the one or more patient optical targets and the one or more transducer optical targets being in data communication with an optical tracker unit, the transducer probe being in data communication with the 3D ultrasound processor and being configured to detect locations of one or more vertebrae of the patient, the image processing system having an image registration module, a 3D visualization module, and an algorithm module, the method comprising:

attaching one or more patient optical targets to desired positions on the patient's body;

detecting locations of the one or more patient optical targets via the optical tracker unit;

detecting a location of the transducer probe via the one or more transducer optical targets and the optical tracker unit;

moving the transducer probe over at least a portion of the patient's body to collect spinal image data while the patient is moving through space to collect one or more of flexion, extension, and rotation image data of the one or more vertebrae;

tracking the movement of the patient via the patient optical targets attached to the patient's body;

generating 3D image data via the 3D ultrasound processor;

sending 3D image data to the image processing system; and processing 3D image data via the image processing system, wherein the processing comprises:
sending 3D image data to the image registration module,
correlating a position of the transducer probe relative to a position of the patient in space and to image data of the one or more vertebrae relative via the image registration module,
correlating images of the spine in different positions to a common reference point via the image registration module;
coordinating a flow of 3D image data through the image processing system, the optical tracker unit, the 3D ultrasound processor, the video capture card, the image registration module, a 3D visualization module of the image processing system, and a database via the algorithm module, and
displaying the real-time 3D image of the one or more vertebrae on the display via the 3D visualization module of the processing system to allow a healthcare provider to assess spinal health and treatment effectiveness based on the displayed real-time 3D image.

16. The method of claim 15, wherein coordinating the flow of image data via the algorithm module comprises one or more of coordinating data inputs from the optical tracker module, delivering resolved images to a 3D visualization module of the image processing system, polling of a database for previously acquired images of the one or more vertebrae, and sending image data to the database for storage.

17. The method of claim 15, further comprising recalling previous image data of the patient's spine stored in a database, and automatically matching current image data with the previous image data to a common reference point via the image registration module to allow the healthcare provider to assess the one or more vertebrae over time.

18. A method for assessing spinal health and treatment effectiveness for spinal conditions of a patient via use of an ultrasonagraphic system, the ultrasonagraphic system having one or more patient optical targets that are attachable to a patient's body, a transducer probe having one or more transducer optical targets, an optical tracker unit, an image processing system, a 3D ultrasound processor, and a display, the one or more patient optical targets and the one or more transducer optical targets being in data communication with an optical tracker unit, the transducer probe being in data communication with the 3D ultrasound processor and being configured to detect locations of one or more vertebrae of the patient, the image processing system having an image registration module, a 3D visualization module, and an algorithm module, the method comprising:

attaching one or more patient optical targets to desired positions on the patient's body;

detecting locations of the one or more patient optical targets via the optical tracker unit;

detecting a location of the transducer probe via the one or more transducer optical targets and the optical tracker unit;

moving the transducer probe over at least a portion of the patient's body to collect spinal image data while the patient is moving through space to collect one or more of flexion, extension, and rotation image data of the one or more vertebrae;

tracking the movement of the patient via the patient optical targets attached to the patient's body;

generating 3D image data via the 3D ultrasound processor;

sending 3D image data to the image processing system; and processing 3D image data via the image processing system, wherein the processing comprises:
sending 3D image data to the image registration module,
correlating a position of the transducer probe relative to a position of the patient in space and to image data of the one or more vertebrae relative via the image registration module,
correlating images of the spine in different positions to a common reference point via the image registration module;
coordinating a flow of 3D image data through the image processing system, the optical tracker unit, the 3D ultrasound processor, the video capture card, the image registration module, a 3D visualization module of the image processing system, and a database via the algorithm module, and
displaying the real-time 3D image of the one or more vertebrae on the display via the 3D visualization module of the processing system to allow a healthcare provider to assess spinal health and treatment effectiveness based on the displayed real-time 3D image, wherein coordinating the flow of image data via the algorithm module comprises one or more of coordinating data inputs from the optical tracker module, delivering resolved images to a 3D visualization module of the image processing system, polling of a database for previously acquired images of the one or more vertebrae, and sending image data to the database for storage.

* * * * *